US008208148B2

(12) United States Patent
Lengsfeld et al.

(10) Patent No.: US 8,208,148 B2
(45) Date of Patent: Jun. 26, 2012

(54) METHOD FOR DETERMINING A CHARACTERISTIC PARAMETER OF A CRP SPECIMEN

(75) Inventors: Hauke Lengsfeld, Helmste (DE); Peter Sander, Bremen (DE); Hans Marquardt, Fredensberg (DE); Rudolf Duwald, Bremervoerde (DE)

(73) Assignee: Airbus Deutschland GmbH, Hamburg (DE)

( * ) Notice: Subject to any disclaimer, the term of this patent is extended or adjusted under 35 U.S.C. 154(b) by 341 days.

(21) Appl. No.: 12/308,013

(22) PCT Filed: Jul. 20, 2007

(86) PCT No.: PCT/EP2007/057533
§ 371 (c)(1),
(2), (4) Date: Dec. 3, 2009

(87) PCT Pub. No.: WO2008/009748
PCT Pub. Date: Jan. 24, 2008

(65) Prior Publication Data
US 2010/0065760 A1    Mar. 18, 2010

Related U.S. Application Data

(60) Provisional application No. 60/832,181, filed on Jul. 20, 2006.

(30) Foreign Application Priority Data

Jul. 20, 2006    (DE) .......................... 10 2006 033 663

(51) Int. Cl.
*G01N 21/00*    (2006.01)

(52) U.S. Cl. ...................................................... 356/445
(58) Field of Classification Search .......... 356/445–448
See application file for complete search history.

(56) References Cited

U.S. PATENT DOCUMENTS

| | | | |
|---|---|---|---|
| 3,570,303 A | | 3/1971 | Nathan et al. |
| 5,457,319 A | * | 10/1995 | Moe et al. ................ 250/339.12 |
| 5,963,660 A | | 10/1999 | Koontz et al. |
| 6,560,248 B1 | * | 5/2003 | Vernackt .......................... 372/18 |
| 7,130,040 B2 | * | 10/2006 | Lindgren et al. .............. 356/300 |
| 7,513,964 B2 | * | 4/2009 | Ritter et al. ....................... 156/64 |
| 2003/0048440 A1 | * | 3/2003 | Lindgren et al. .............. 356/300 |
| 2005/0025350 A1 | | 2/2005 | Engelbart et al. |
| 2005/0047643 A1 | | 3/2005 | Lowe |

(Continued)

FOREIGN PATENT DOCUMENTS

DE    690 06 213 T 2    5/1994
(Continued)

OTHER PUBLICATIONS

International Search Report for PCT/EP2007/057533.
(Continued)

*Primary Examiner* — Michael P Stafira
(74) *Attorney, Agent, or Firm* — Husch Blackwell LLP

(57) ABSTRACT

The invention relates to a method for determining at least one characteristic parameter of a CRP specimen (3, 4), in particular a specimen of prepreg material, for aerospace, comprising the following method steps: presenting the specimen (3, 4), irradiating the. specimen (3, 4) with a predetermined spectrum of electromagnetic radiation, recording the interaction between the specimen (3, 4) and the electromagnetic radiation in a data record (20) and determining the at least one characteristic parameter from the recorded data record (20).

10 Claims, 4 Drawing Sheets

U.S. PATENT DOCUMENTS

2005/0117793 A1 * 6/2005 Engelbart et al. ............. 382/141

FOREIGN PATENT DOCUMENTS

| DE | 19912723 | 11/2000 |
| --- | --- | --- |
| DE | 10 2004 035 208 B3 | 9/2005 |
| EP | 1484165 | 12/2004 |
| JP | 61-245045 | 10/1986 |
| JP | 2001-012932 | 1/2001 |
| JP | 2001-188906 | 7/2001 |
| JP | 2002-069668 | 3/2002 |
| JP | 2003-149160 | 5/2003 |
| JP | 2006 064531 A | 3/2006 |
| JP | 2006-64531 A | 3/2006 |
| RU | 94019480 A1 | 6/1996 |
| WO | WO 94/15197 | 7/1994 |
| WO | WO2005/036146 A1 | 4/2005 |

OTHER PUBLICATIONS

German Search Report for DE 10 2006 033 663.1.
Russian Decision on Granting for related patent app. No. 2009105043/05(006763).
Prakash; Non-destructive Testing of Composites, IPC Business Press Limited 1980, p. 217-226.
Summary of the Office Action(Notice of Reasons for Refusal) of related JP App. No. 2009-519994.

* cited by examiner

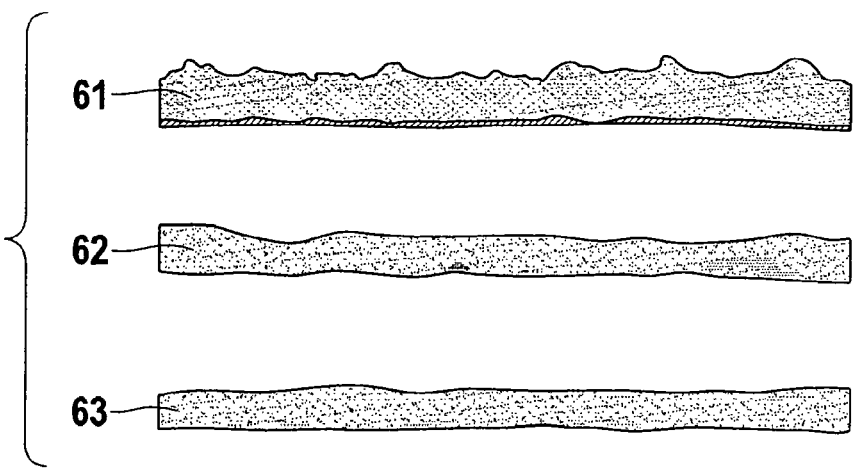
Fig. 6
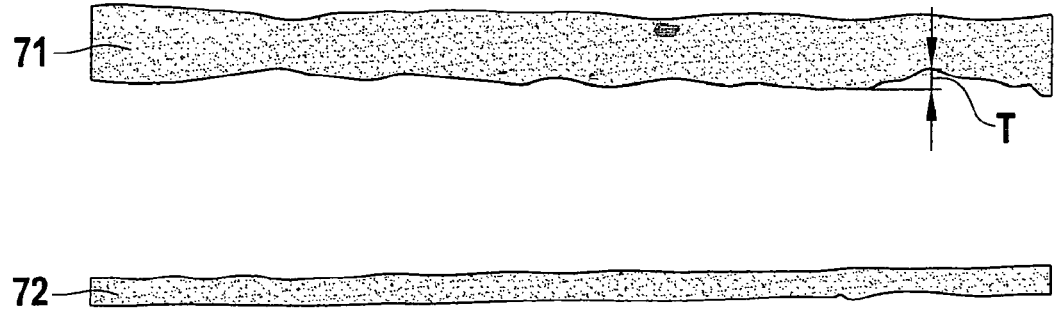
Fig. 7

METHOD FOR DETERMINING A CHARACTERISTIC PARAMETER OF A CRP SPECIMEN

The present invention relates to a method for determining at least one characteristic parameter of a CRP specimen, in particular a specimen of prepreg material, for aerospace.

Although it can be applied to specimens of any desired carbon fiber reinforced plastic (CRP), the present invention and the problems on which it is based are explained in more detail with reference to specimens of unidirectional (UD) prepreg material.

Specifically in the area of aerospace, large CRP components produced from UD prepreg material are increasingly being used because of their high strength along with low weight. UD prepreg material refers to semifinished products comprising continuous fibers and an uncured thermosetting polymer matrix, wherein the continuous fibers may extend both in the x direction and in the y direction. This extension covers both UD materials and woven material. The quality of the UD prepreg material used, which can be described. for example by the parameters of air content, surface finish or resin distribution, is decisive for the reliability, in particular the strength, of the large CRP components to be produced. To this extent, checking the quality of the UD prepreg material before it is processed is imperative.

A procedure known as the water pickup test for determining the degree of waterproofing or impregnation of UD prepreg material is generally known. For this purpose, a specimen of UD prepreg material is initially weighed and clamped between two plates in such a way that a strip of specimen 15 mm wide protrudes. This arrangement is suspended in the direction of the fibers in a water bath for 5 minutes. After removing the plates, the specimen is again weighed. The difference in weight is used as a measured value for the degree of impregnation. The smaller the amount of water picked up, the higher the degree of waterproofing or impregnation.

A disadvantage of the water pickup test procedure has been found to be the fact that it does not allow any conclusions to be drawn for example concerning the resin distribution in the UD prepreg material or the surface finish of the UD prepreg material. The water pickup test procedure merely provides information of an overall effect, it not being possible to differentiate between the individual influencing variables or characteristic parameters.

Against this background, the present invention is based on the object of providing an improved method for determining at least one characteristic parameter of a CRP specimen, in particular a specimen of prepreg material, for aerospace.

This object is achieved according to the invention by a method with the features of Patent Claim 1.

Accordingly, method for determining at least one characteristic parameter of a CRP specimen, in particular a specimen of prepreg material, for aerospace is provided, comprising the following method steps: presenting the specimen, irradiating the specimen with a predetermined spectrum of electromagnetic radiation, recording the interaction between the specimen and the electromagnetic radiation in a data record and determining the characteristic parameter from the recorded data record.

Consequently, the present invention has the advantage over the approach mentioned at the beginning that at least one characteristic parameter of the specimen can be determined by means of the method. In the case of the method according to the invention, it is consequently not information of an overall effect that is determined, but a specific property of the specimen directly. The knowledge of such characteristic parameters allows a much more accurate finding to be reached, for example concerning the likely strength of the component produced from the CRP. Furthermore, it is easier for the manufacturer of the CRP material to eliminate defects, since the cause of defects, for example excessive air content in the CRP, can be easily determined by means of the method according to the invention.

Advantageous refinements and improvements of the present invention can be found in the subclaims.

A data record is to be understood in this patent application as also meaning any kind of image.

According to a preferred development of the invention, the electromagnetic radiation that has interacted with the specimen is passed through a microscope before the recording of the data record. Consequently, the resolution of the data record can be advantageously increased by means of the microscope, which increases the accuracy of the characteristic parameter to be determined.

In the case of a further preferred exemplary embodiment, the spectrum of the electromagnetic radiation is chosen in the range of visible light. This leads to a very simple method. Alternatively, however, any other type of radiation may also be used, such as for example UV light or X-rays, to make improved recording of the constituent parts of the specimen possible, that is to say for example an air content and/or resin content, or to improve differentiability of the constituent parts.

According to a further preferred development of the invention, the data record is recorded with the aid of a CCD camera and stored in a memory device. This makes very easy recording possible and makes it easier to present the data record to an evaluation device downstream of the memory device for evaluating the data record.

According to a further preferred exemplary embodiment of the invention, intensities assigned to different surface regions of the specimen, of the radiation that has interacted with these surface regions, are recorded in the data record. The specimen has one or more surface regions, which differ in how they are made up, that is to say, for example, an air content in the respective surface region or the respective surface finish, in such a way that radiation impinging on the specimen is reflected with different intensities. The at least one characteristic parameter can be determined on the basis of the different intensities.

Alternatively, the wavelengths of the radiation in interaction with the specimen could also be analysed to ascertain the at least one characteristic parameter.

According to a further preferred development of the invention, the characteristic parameter describes an air content in the specimen, a resin content in the specimen, a surface finish of the specimen, a depth of roving interfaces in the specimen, an air distribution in the specimen and/or a resin distribution in the specimen. The properties mentioned here are of great significance for the reliability, in particular the strength, of the component to be produced that is associated with the specimen.

Preferably, the assigned intensities coinciding with a predetermined intensity range are added together to determine the air content and/or the resin content in the specimen. This allows the air content per unit area in the surface of the specimen that is under investigation to be determined in a very simple way. On the basis of the air content or resin content per unit area, an air content by volume and/or air content by weight or resin content by volume and/or resin content by weight in the specimen can be ascertained in a very simple way.

According to a further preferred exemplary embodiment of the invention, the assigned, intensities coinciding with a predetermined intensity range are analysed for their homogeneous distribution with respect to the different surface regions to determine the resin distribution and/or air distribution in the specimen. For this purpose, the surface of the specimen that is to be investigated is subdivided for example into the number of different surface regions and the resin content and/or air content is determined in the respective surface regions. Subsequently, a variance of the resin contents and/or air contents is calculated, allowing a homogeneous/inhomogeneous distribution of the resin and/or the air to be ascertained.

According to a further preferred development of the invention, a comparison of the recorded data record with one or more reference data records is performed, the characteristic parameter being made equal to a predetermined value in dependence on the reference data record that substantially coincides with the recorded data record. This method step makes it possible in a very simple way to categorize the data records recorded. For example, the characteristic parameter assigned to a recorded data record can be given the values 1, 2 or 3, with 1 corresponding to an inadequate surface finish, 2 corresponding to an adequate surface finish and 3 corresponding to a good surface finish.

The reference data records are preferably used as a measure of the air content in the specimen, the resin content in the specimen, the surface finish of the specimen, the resin distribution and/or air distribution in the specimen, and/or the depth of roving interfaces in the specimen. Reference data records, which correspond for example to an air content of 1, 5 or 7% air content in the specimen, can then be advantageously compared with the recorded data record, the characteristic parameter then being assigned the values 1, 5 or 7.

In the case of a further preferred exemplary embodiment of the invention, the at least one characteristic parameter is differently weighted in accordance with the scale used. For example, the resin content and the surface finish of the specimen, both possible characteristic parameters of the specimen, have a more or less strong influence on the quality of the specimen investigated. Weighting is a simple means of allowing for this fact.

Preferably, a number of characteristic parameters are determined, weighted and added together, the sum being used as a measure of the quality of the specimen. The quality determined in this way can be very informative with respect to the likely strength of the material associated with the specimen.

According to a further preferred development of the invention, the specimen is taken from the same portion of material as other specimens being tested by the water pickup test procedure, the at least one characteristic parameter being assigned to a result from the water pickup test procedure. This advantageously allows a correlation of the results of the method according to the invention with the water pickup test procedure. This is advantageous for standardizing the quality or results to be achieved from the respective test procedures.

According to a further preferred development of the invention, a cross section of the specimen is irradiated with the electromagnetic radiation. The cross section advantageously reveals the internal composition of the specimen. The cross section preferably runs transversely to the direction of the fibers. Such a cross section provides a clear view of surface regions between the individual fibers, which have a great influence on the quality of the component to be produced.

Generally, all the evaluating operations mentioned here, such as for example the determination or comparison, can be carried out by means of an evaluation device, in particular a computer device.

The invention is explained in more detail below on the basis of exemplary embodiments with reference to the accompanying figures of the drawing, in which:

FIG. 6 shows two still further reference data records, which describe the surface finish of a reference specimen, according to the exemplary embodiment; and FIG. 7 shows two still further reference data records, which describe the depth of roving interfaces, according to the exemplary embodiment.

In all the figures of the drawings, elements that are the same or functionally the same have in each case been provided with the same reference numerals, unless otherwise indicated.

Figure 1:
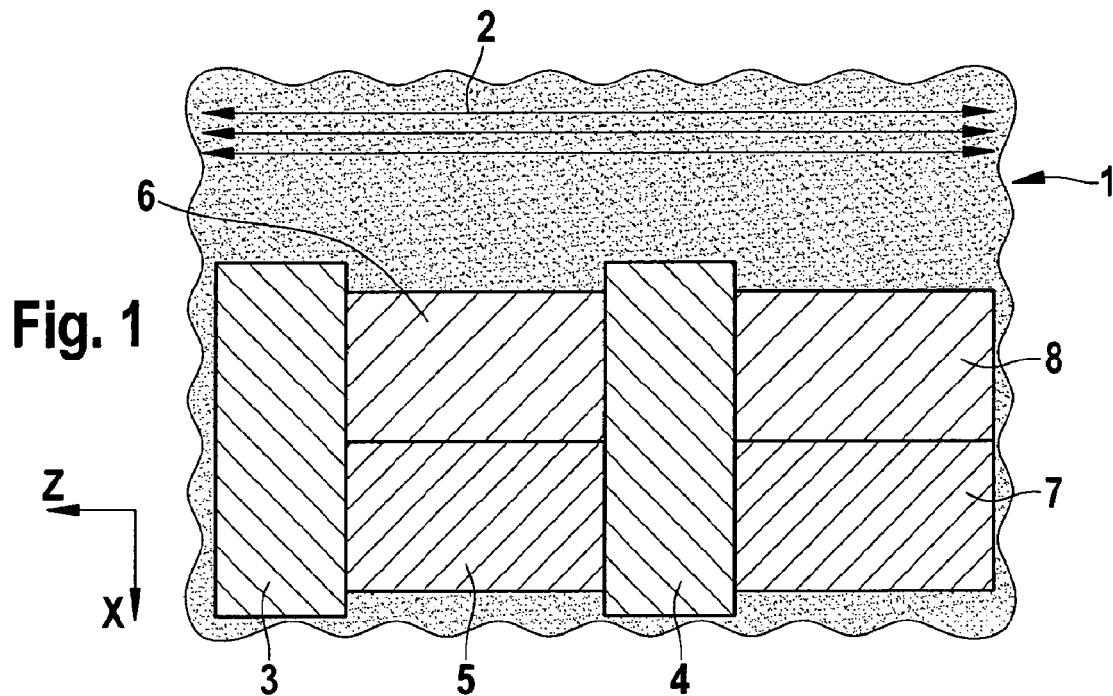
FIG. 1 shows a state of the method when taking a specimen according to an exemplary embodiment of the present invention.

FIG. 1 shows a first state of the method when taking a specimen, given by way of example, according to an exemplary embodiment of the present invention. A sheet-like portion of material 1 of a UD prepreg material is provided in a first method step. The fibers of the portion of material 1 preferably extend in the direction denoted by 2. A number of specimens are taken from the portion of material 1.

The specimens 3 to 8 are cut out from the portion of material 1 with the aid of suitable templates. With preference, the specimens 3, 4 are of an approximately rectangular form, their longitudinal side running transversely to the direction of the fibers 2. By contrast, the longitudinal side of the substantially rectangular specimens 5 to 8 extends in the direction of the fibers.

Figure 2:
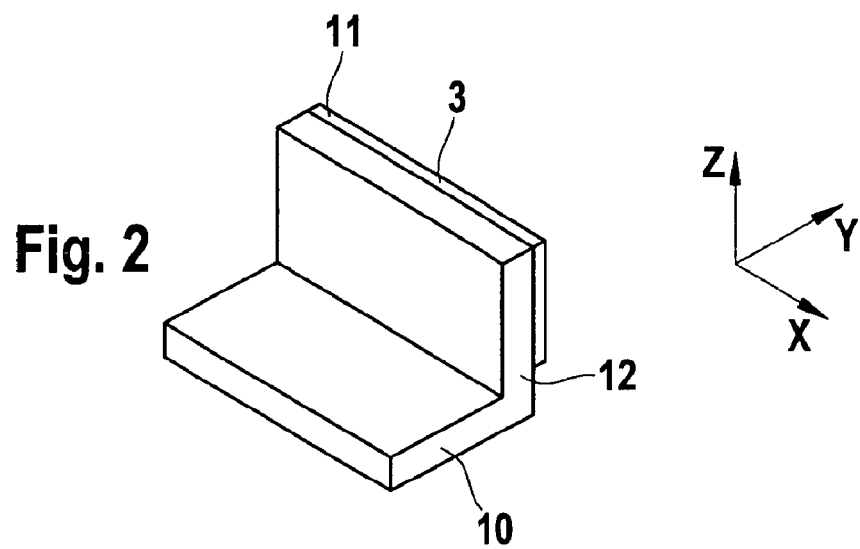
FIG. 2 shows a further state of the method when mounting the specimen on a specimen holder according to the exemplary embodiment.

As shown in FIG. 2, the specimen 3 is mounted in a sheet-like manner on a specimen holder 10. The fibers of one side face 11 of the specimen 3 in this case run in the Z direction, that is to say perpendicular to the side face 11. The specimen holder 10 is formed here as an angle, the specimen 3 being mounted flat against one leg 12 of the angle.

Figure 3A:
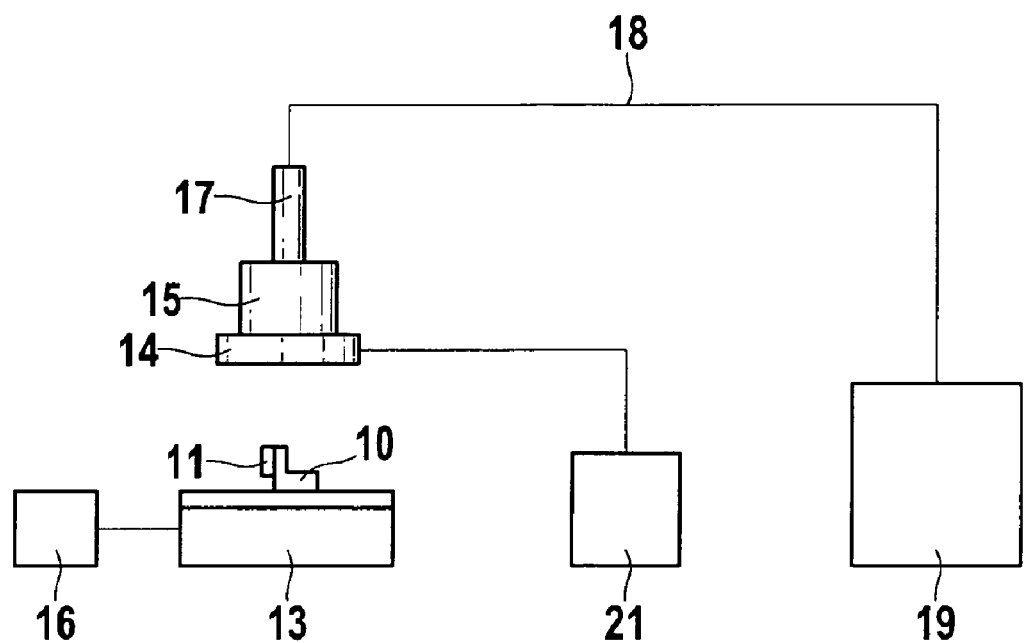
FIG. 3A shows yet another state of the method when determining at least one characteristic parameter of the specimen according to the exemplary embodiment.

Subsequently, according to the exemplary embodiment, the specimen holder 10 with the specimen 3 is arranged on a travelling table 13, as shown in FIG. 3A. By means of a controller 16, which is designed for moving the travelling table 13 in the xy plane, the specimen is positioned underneath an arrangement comprising a ring light 14, a microscope 15 and a charge-coupled device (CCD) camera 17. The positioning is preferably performed in an automated manner.

A cold light source 21 supplies the ring light 14 with radiation, for example white light. The radiation given off by the ring light 14 impinges on the side face 11 of the specimen 3 and is reflected into the microscope 15, whereupon it is recorded by the CCD camera 17 connected to the microscope.

In dependence on the radiation recorded, the CCD camera generates an electronic data record 20, which is fed by means of a cable 18 to a computer unit 19, the fed data record 20 being stored in a memory device and subsequently evaluated by an evaluation unit of the computer unit 19.

Figure 3B:
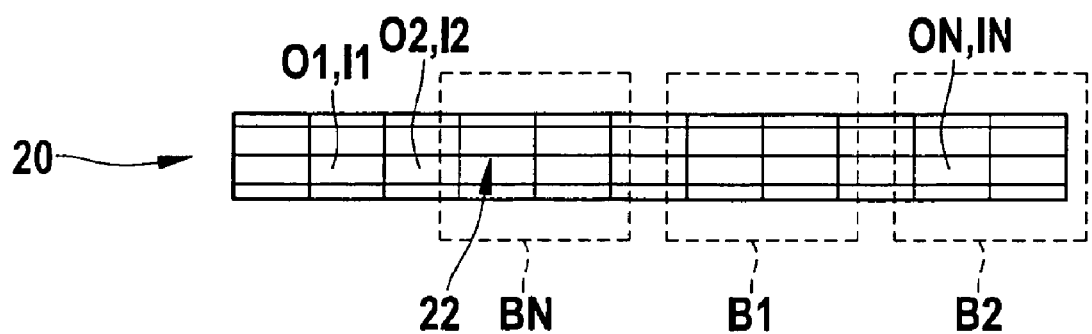
FIG. 3B shows yet another state of the method when determining the characteristic parameter according to the exemplary embodiment.

FIG. 3B shows a data record 20 by way of example. The data of the data record 20 that are assigned to the side face 11 take the form of a grid 22. The grid 22 thereby defines data positions O1, O2, . . . ON assigned to surface regions of the same size of the side face 11. Intensities I1, I2, . . . IN of the light reflected by the surface regions and recorded by the CCD camera are stored at each of the data positions O1, O2, . . . ON. Consequently, the recorded data record 20 can be presented for example in various shades of grey from white to black.

In order then for example to determine the air content in the side face 11, the assigned intensities coinciding with a predetermined intensity range are added together. Alternatively or in addition, it may also be provided that the data positions O1, O2, . . . ON that have the coinciding assigned intensities are counted. To determine the predetermined intensity range, for example such a grey area that corresponds to the air in the side face 11, a calibration may be performed in advance on the basis of a reference specimen.

Since a resin content can be assigned different intensities I1, I2, . . . IN of the radiation, the resin contents can be easily distinguished from the air contents. The determination of the resin content differs from the determination of the air content merely by a different predetermined intensity range.

In order to determine a resin distribution and/or air distribution in the specimen, ranges B1, B2, . . . BN, which respectively have an equal number of data positions O1, O2, . . . ON, are defined for example. The resin content and/or air content in the respective range B1, B2, . . . BN is determined by the method described above. A variance of the air content with respect to the ranges B1, B2, . . . BN corresponds to the homogeneity/inhomogeneity of the distribution of the resin and/or the air in the specimen.

Alternatively, a comparison of the recorded data record 20 with reference data records may also be performed, as shown in FIGS. 4 to 7.

Figure 4:
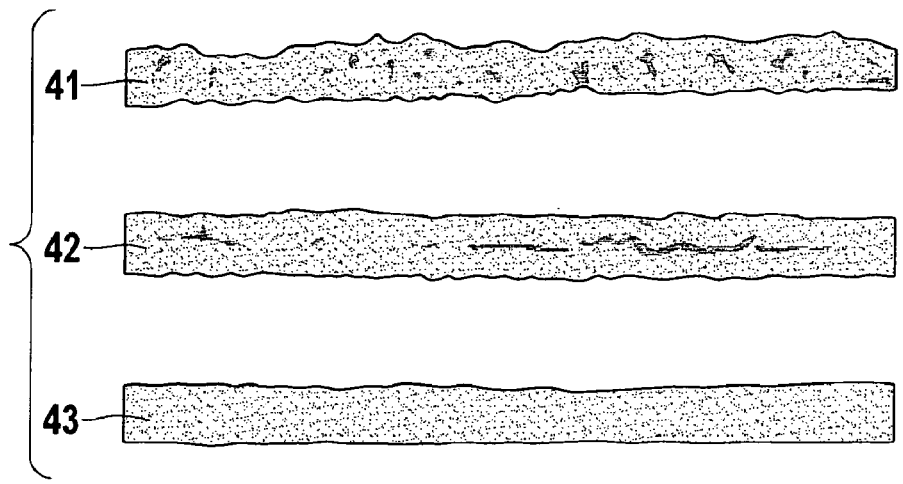
FIG. 4 shows two reference data records, which describe an air distribution and/or an air content of a reference specimen, according to the exemplary embodiment.

FIG. 4 shows reference data records by way of example, that is to say images 41, 42, 43 of reference specimens, which have an excessive air content of approximately 16%, an acceptable air content of approximately 6% and a preferred air content of approximately 1%. The recorded data record 20 is compared with the reference data records 41, 42 and 43 by a comparison device of the computer unit 19. Depending on with which reference data record 41, 42 or 43 the recorded data record 20 best coincides, the characteristic parameter that describes the air content in the specimen is assigned for example the value 1, 2 or 3, respectively.

Figure 5:
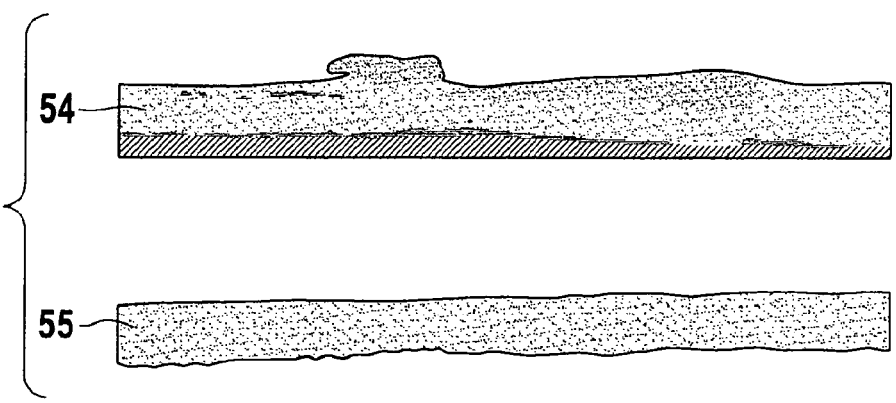
FIG. 5 shows two further reference data records, which describe a resin distribution and/or a resin content in a reference specimen, according to the exemplary embodiment.

FIG. 5. shows further reference data records 54, 55 by way of example, the reference data record 54 corresponding to a very nonuniform resin distribution in a reference specimen and the reference data record corresponding to an acceptable uniform resin distribution in a reference specimen. In a way corresponding to the method as shown in FIG. 4, the characteristic parameter that describes the resin distribution in the specimen is allocated a value.

FIG. 6 shows three further reference data records 61, 62, 63 by way of example, describing the characteristic parameter of the surface finish. The reference data records 61, 62, 63 respectively describe an unacceptable surface finish, an acceptable surface finish and a preferred surface finish of a reference specimen. The determination of the characteristic parameter for the surface finish is in this case performed in a way analogous to the method as explained in relation to FIG. 4.

FIG. 7 shows reference data records 71, 72 by way of example, the reference data record 71 corresponding to a specimen with unacceptable roving interfaces and the reference data record 72 corresponding to a specimen with acceptable roving interfaces. The roving interfaces typically occur in the production of the prepreg material. The characteristic parameter that describes the depth T of the roving interfaces is determined in a way analogous to the method as described for FIG. 4.

Subsequently, the respective characteristic parameters may be differently weighted in accordance with their significance for the quality of the specimen, the quality relating for example to a strength of the component to be produced. Subsequently, the weighted, characteristic parameters are added together, the sum being used as a measure of the quality of the specimen. It goes without saying that any other mathematical operation is conceivable for determining a value for the quality of the specimen that is as informative as possible. The value determined for the quality can be used as a basis for decisions, for example for returning prepreg material to the manufacturer or for processing the prepreg material in less high-value components.

The specimens 5, 6, 7, 8 may be tested by the water pickup test procedure, the results from this test procedure being assigned to the determined value for the quality of the specimens 3 and 4—for example a degree of impregnation of 5 that has been determined in accordance with the water pickup test procedure corresponds to a quality in the range from 20 to 30 that has been determined by the method according to the invention. As a result, a certain comparability between the different test procedures is made possible, even though the method according to the invention is significantly more accurate.

The invention is not restricted to the specific method represented in the figures for determining at least one characteristic parameter of a CRP specimen, in particular a specimen of prepreg material, for aerospace.

Rather, the individual sequence of individual method steps of the method according to the invention can be changed in various ways. The form taken by the individual method steps can also be modified.

For example, a specimen may also have side faces running obliquely to the direction of the fibers that are analysed in the method according to the invention.

Full automation of the method according to the invention, that is to say for example of the positioning process of the specimen underneath the CCD camera or else the taking of specimens, is to be preferred over a manual solution.

It goes without saying that the invention can also be applied to specimens, for example CRP specimens, with fibers which extend in different directions.

Furthermore, the analysis of specimens of different materials, in particular fiber reinforced materials, such as GLARE, is also possible by means of the method according to the invention.

LIST OF REFERENCE NUMERALS 1 portion of material
2 direction of fibers
3 specimen
4 specimen
5 specimen
6 specimen 7 specimen
8 specimen
10 specimen holder
11 side face
12 leg
13 travelling table
14 ring light
15 microscope
16 controller
17 CCD camera
18 cable
19 computer unit
20 data record
21 cold light source
22 grid
41 ... 72 reference data records
T depth of the roving interfaces
O1, O2, ... ON data positions
I1, I2, ... IN intensities
B1, B2, ... BN ranges

The invention claimed is:

1. Method for determining a characteristic parameter of a CRP specimen, in particular a specimen of prepreg material, for aerospace, comprising the following method steps:
providing the specimen;
irradiating the specimen with a spectrum of electromagnetic radiation;
recording an interaction intensity between the specimen and the electromagnetic radiation in a data record; and
identifying the characteristic parameter from the data record,
wherein said interaction intensities assigned to different regions of the specimen, are recorded in the data record,
wherein the characteristic parameter comprises at least two of an air content in the specimen, a resin content in the specimen, a surface finish of the specimen, a depth of roving interfaces in the specimen, an air distribution in the specimen and a resin distribution in the specimen, and
wherein said assigned interaction intensities coinciding with a predetermined intensity range are added together to determine at least one of the air content, and the resin content in the specimen.

2. The method according to claim 1
wherein said assigned interaction intensities coinciding with a predetermined intensity range are analyzed to determine at least one of the resin distribution and air distribution with respect to their homogeneous distribution in the different regions of the specimen.

3. The method according to claim 1, wherein the electromagnetic radiation that has interacted with the specimen is passed through a microscope before the recording of the data record.

4. The method according to claim 1, wherein the spectrum of the electromagnetic radiation is chosen in the range of visible light.

5. The method according claim 1, wherein the data record is recorded with the aid of a CCD camera and stored in a memory device.

6. The method according to claim 1, wherein the recorded data record is compared with one or more reference data records, the at least one characteristic parameter being made equal to a predetermined value in dependence on the reference data record that substantially coincides with the recorded data record.

7. The method according to claim 6, wherein the reference data records are used as a measure of at least one of the air content in the specimen, the resin content in the specimen, the surface finish of the specimen, the resin distribution and air distribution in the specimen and/or the depth of roving interfaces in the specimen.

8. The method according to claim 7, wherein the characteristic parameter is differently weighted in accordance with the scale used.

9. The method according to claim 8, wherein a number of characteristic parameters are determined, weighted and added together, the sum being used as a measure of the quality of the specimen.

10. The method according to claim 1, wherein a side face of the specimen is irradiated with electromagnetic radiation, CRP fibers running substantially perpendicular to the side face.

* * * * *